US007608754B2

(12) United States Patent
Weyens et al.

(10) Patent No.: US 7,608,754 B2
(45) Date of Patent: Oct. 27, 2009

(54) DOUBLE FRUCTAN BEETS (75) Inventors: Guy Weyens, Beersel (BE); Jean Lathouwers, Machelen (BE); Cornelius (Kees) Van Dun, De Lier (NL)

(73) Assignee: SES Europe N.V./S.A., Tienen (BE)

( * ) Notice: Subject to any disclaimer, the term of this patent is extended or adjusted under 35 U.S.C. 154(b) by 329 days.

(21) Appl. No.: 10/415,686

(22) PCT Filed: Jun. 25, 2002

(86) PCT No.: PCT/US02/19860

§ 371 (c)(1),
(2), (4) Date: Sep. 22, 2003

(87) PCT Pub. No.: WO03/000854

PCT Pub. Date: Jan. 3, 2003

(65) Prior Publication Data

US 2004/0064852 A1 Apr. 1, 2004

Related U.S. Application Data (60) Provisional application No. 60/300,741, filed on Jun. 25, 2001.

(51) Int. Cl.
C12N 15/82 (2006.01)
C12N 15/54 (2006.01)
C12N 15/11 (2006.01)
A01H 5/00 (2006.01)
(52) U.S. Cl. .................. 800/284; 800/278; 800/298; 435/320.1; 435/468; 435/193; 536/23.1; 536/23.2; 536/23.6
(58) Field of Classification Search ................. 800/298
See application file for complete search history.

(56) References Cited

U.S. PATENT DOCUMENTS

| 5,986,173 | A | 11/1999 | Smeekens |
| 6,025,542 | A | 2/2000 | Smeekens |
| 6,057,494 | A | * 5/2000 | Koops et al. ............. 800/284 |
| 6,147,280 | A | 11/2000 | Smeekens et al. |

FOREIGN PATENT DOCUMENTS

| AU | 9511554 | 7/1995 |
| DE | 4330960 | 3/1993 |
| NL | 9401140 | 7/1994 |
| NL | 1000064 | 4/1995 |
| WO | PCT/US89/02729 | 12/1989 |
| WO | PCT/NL96/00012 | 1/1992 |
| WO | PCT/EP93/02110 | 3/1994 |
| WO | PCT/EP94/03031 | 3/1995 |
| WO | WO 95/13389 | * 5/1995 |
| WO | PCT/EP95/05091 | 6/1996 |
| WO | WO 98/39460 A1 | 9/1998 |
| WO | WO 99/54480 A1 | 10/1998 |
| WO | WO 99/46395 A1 | 9/1999 |

OTHER PUBLICATIONS

Vergauwen et al Plant Physiology 2003, 133:391-401.*
Turk et al 1997 New Phytology 136:29-38.*
Vijn et al 1997 The Plant Journal 11:387-398.*
Smeekens, et al. Fructans and fructan accumulating transgenic plants. Journal of Cellular Biochemistry Supplment, 1994, vol. 0, No. 18 Part A, p. 84.
Ebskamp, et al. Fructan accumulation in transgenic plants, Journal of Cellular Biochemistry Supplement, 1994, vol. 0, No. 18 Part A, p. 119.
Van Der Meer, et al. Cloning of the fructan biosynthesis pathway of Jerusalem artichoke. Plant Journal, 1998, vol. 15, No. 4, pp. 489-500.
Hellwege, et al. Transgenic potato tubers synthesize the full spectrum of inulin molecules naturally occurring in globe artichoke roots. Proc. Nat. Aca. Scil, vol. 97, No. 15, 2000. pp. 8699-8704.
Hellwege, et al. Transgenic potato tubers accumulate high levels of 1 kestose and nytose. Plant Journal, 1997, vol. 12, No. 5, pp. 1057-1065.
Sprenger, et al. Fructan synthesis in transgenic tobacco and chicory plants expressing barley surcrose. FEBS Letters, vol. 400, No. 3 pp. 355-358, 1997.
Sevenier, et al. High level fructan accumulation in a transgenic sugar bet. Nature Biotechnology, 1998, vol. 16, No. 9, pp. 843-846.
Vijn, et al. Cloning of sucrose:sucrose 1 fructosyltranferase from onion and synthesis of structurally defined fructan molecules from sucrose. Plant Physiology, 1998, vol. 117.
Van De Meer, et al. Fructan as a new carbohydrate sink in transgenic potato plants. The Plant Cell, Apr. 1994, vol. 6, No. 4, pp. 561-570.
Ruff, et al. Production of fructan in plans by expression of a bacterial fructan polymerase. Plant Physiology, 1994, vol. 105, N. 1 Suppl., p. 116.
R.A. Rastall, et al; *Synthesis of Oligosaccharides by Reversal of a Fungal B- Glucanase*; Biotechnology Letters, vol. 14, No. 5, pp. 337-378, May 1992.
Robert Sevenier, et al; *High Level Fructan Accumulation in a Transgenic Sugar Beet*, Nature Biotechnolgy, vol. 16, pp. 1-5, Sep. 1998.
Teruaki Shiroza & Howard Kuramitsu; *Sequence Analysis of the Streptococcus Mutans Fructosyltransferase Gene and Flanking Regions*; Jouranl of Bacteriology, pp. 810-816, Feb. 1988.
Urs Simmen, et al; *Fructan Synthesis in Excised Barley Leaves*; Plant Physiology, vol. 101, pp. 459-468, 1993.
M. Luscher, et al; *Purification and Characterization of Fructan: Fructan Fructosyltransferase from Jerusalem Artichoke*; New Phytol., vol. 123, pp. 717-724, 1993.
Pierre Bancal, et al; *Fructan Chemical Structure and Sensitivity to an Exhohydrolase*; Carbohydrate Research, vol. 217, pp. 137-151, 1991.

(Continued)

Primary Examiner—Russell Kallis
Assistant Examiner—Brent Page
(74) Attorney, Agent, or Firm—Christensen O'Connor Johnson Kindness PLLC (57) ABSTRACT The present invention relates to fructan producing plants particularly to methods for the production of fructans having a low degree of polymerization. The invention is also directed to non-fructan producing plants which are transformed or crossed to contain at least two of three genes encoding a fructosyltransferase.

8 Claims, 5 Drawing Sheets

OTHER PUBLICATIONS

N.J. Chatterton, et al; *Structures of Fructan Oligomers in Orchardgrass*; J. Plant Physiol.; vol. 142, pp. 552-556, 1993.

I. Vijn, et al; *Fructan of the Inulin Neoseries is Synthesized in Transgenic Chicory Plants Harbouring Onion Fructan; Fructan 6G-fructosyltranserase*; The Plant Journal; vol. 11(3), pp. 387-398, 1997.

Meiji Seika Kaisha; *Bifidus growth-stimulating substances*; Chemical Abstracts, vol. 100, pp. 508, Apr. 23, 1984.

De Roover, J., et al., "Drought Induces Fructan Synthesis and 1-SST (Sucrose:Sucrose Fructosyltransferase) in Roots and Leaves of Chicory Seedlings (*Cichorium intybus* L.)," Planta. 210(5):808-814, Apr. 2000. (Abstract only.).

Luscher, M., et al., "Cloning and Functional Analysis of Sucrose:Sucrose 1-Fructosyltransferase From Tall Fescue," Plant Physiol. 124(3):1217-1228, Nov. 2000. (Abstract only.).

Pavis, N., et al., "Fructans and Fructan-Metabolizing Enzymes in Leaves of Lolium Perenne," New Phytologist 150:97-109, 2001.

Shiomi, N., "Purification and Characterisation of 6G-Fructosyltransferase From the Roots of Asparagus (*Asparagus officinalis* L.)," Carbohydrate Research (Netherlands) 96(2):281-292, Oct. 1981. (Abstract only.).

Simmen, U., et al., "Fructan Synthesis in Excised Barley Leaves," Plant Physiol. 101:459-468, 1993.

Van Den Ende, W., et al., "Cloning, Developmental, and Tissue-Specific Expression of Sucrose:Sucrose 1-Fructosyl Transferase From Taraxacum Officinale. Fructan Localization in Roots," Plant Physiology 123:71-79, May 2000.

Wei, J.-Z., and N. Jerry Chatterton, "Fructan Biosynthesis and Fructosyltransferase Evolution: Expression of the 6-SFT (Sucrose:Fructan 6-Fructosyltransferase) Gene in Crested Wheatgrass (*Agropyron cristatum*)," Journal of Plant Physiology 158(9):1203-1213, 2001. (Abstract only.).

Wei, J.-Z., et al., "Linkage Mapping and Nucleotide Polymorphisms of the 6-SFT Gene of Cool-Season Grasses," Genome 43:931-938, 2000.

* cited by examiner

DOUBLE FRUCTAN BEETS

CROSS REFERENCES TO RELATED APPLICATIONS

This application claims the benefit under 35 U.S.C. §371 as a national filing of the international application Number PCT/US02/19860 filed 25 Jun., 2002 and claims the benefit of the U.S. provisional application No. 60/300,741 filed 25 Jun. 2001.

FIELD OF THE INVENTION

The present invention relates to fructan producing plants, particularly to methods for the production of fructans having a low degree of polymerization. The invention is also directed to non-fructan producing plants which are transformed or crossed to contain at least two of three genes encoding a fructosyltransferase.

BACKGROUND OF THE INVENTION

Many biotechnology companies have been interested in developing transgenic plants that would produce fructosyltransferase to facilitate the development of a sugar substitute that is sweet and not hydrolysed in the human stomach or small intestine, and having good organoleptic properties. A desirable substitute would not be degraded or absorbed in to the body, and would provide a much lower energy value than glucose, fructose, or sucrose.

Fructans are non-structural storage carbohydrates. This polymer consists mostly of repeating fructose units. Fructans occur in Monocots such as Poaceae, and Liliaceae, and in some Dicots, such as Compositae.

Fructans have not been commercially useful so far, due to the limited species they occur in and their low level of accumulation in those species. The function of a fructan is determined by the length of the fructan chain and the degree of polymerization (DP) of the monosaccharide. A DP value of 3 would mean that there are three monosaccharides ($G_m F_n$), where G-F is sucrose, G is glucose, and F is fructose. The glycosidic linkage which interconnects the fructose units can be a 2-1 or a 2-6 type, depending on the fructosyltransferase. The function of a fructan depends on its backbone, its DP, and the degree of branching.

Many fructan related patent applications disclose methods designed to produce low calorie sweeteners in plants that normally do not produce fructans. A number of applications report the production of transformed plants having differing degrees of polymerization and total amount of fructosyl and glycosyl residues.

The synthesis of fructans in bacteria is catalysed by one enzyme, levansucrase (Dedonder R). (1966) Levansucrase from *Bacillus subtilis* (Methods in Enzymology 8, 500-505). Bacterial sequences encoding FTF in *S. mutans* and levansucrase in *B. subtilis* are described by Sato and Kurimaitsu (1986). Isolation and characterisation of a fructosyltransferase gene from *Streptococcus mutans* GS-5 (1986). Bacterial genes transformed into host plants were able to facilitate the synthesis of fructans (Van der Meer et al. (1994)). Fructans have also been are described as a new carbohydrate sink in transgenic potato plants (Plant Cell 6, 561-570). An attempt to use the levansucrase gene for enhancing tomatoes was disclosed in WO89/12386, WO94/14970 and U.S. Pat. No. 6,147,280 (the teaching of U.S. Pat. No. 6,147,280 is hereby incorporated by reference) disclose use of the levansucrase encoded by the ftf gene of *S. mutans*, the levansucrase encoded by the SacB gene of *B. subtilus*, the 6-SFT gene from barley, and the FFT gene from Jerusalem artichoke (*Helianthus tuberosus* L) to produce oligosaccharides having 0 or 1 glucose residues and having 2-8 and preferably 2-3 fructose residues.

WO96/21023 describes transforming plant genes encoding 1-SST and 1-FFT individually into petunias and potatoes. This application describes 1-SST and 1-FFT as having essentially different enzymatic properties. 1-FFT was not able to catalyse the initial step of fructan synthesis, and 1-SST was not able to catalyse the formation of fructan polymers with a degree of polymerisation higher than 5. By employing 1-SST activity alone, it was only possible to synthesis oligofructans from sucrose having a degree of polymerization of up to 5. This application did not describe the synthesis of fructans with a higher degree of polymerization using sucrose as a substrate indicating that both 1-SST and 1-FFT are needed for higher degree of polymerization and that 1-FFT activity alone is insufficient to carry out the synthesis of fructans from sucrose.

There is a need for transgenic plants, prepared from plants that do not normally produce fructans, which accumulate higher DP fructans by the elongation of the isokestose produced by 1-SST and/or sucrose. There is also a need for the action of two enzymes which results in the formation of a mixture of fructan molecules with different chain lengths.

BRIEF SUMMARY OF THE INVENTION

The present invention provides a plant capable of producing fructan molecules, which may protect it from environmental stress.

Another objective of the present invention is to produce a transgenic plant, such as maize or sugar beet, that accumulates fructans formed by at least two fructsyltransferases.

The present invention also includes a method of forming low caloric sweeteners in plants that are not degraded during harvest, because the host plant does not have enzymes adapted to degrade fructans.

The present invention addresses a method for producing fructans having several degrees of polymerization, comprising the steps of:

(a) selecting two different nucleic DNA that code respectively for two fructosyltransferase enzymes, which convert at least one substrate into a fructan having a range of degrees of polymerization;

(b) linking the DNA to suitable transcription-initiation and transcription-termination signals to provide an expression construct;

(c) transforming a suitable host plant with the expression construct regenerating a transgenic plant from the transformed plant cell;

(d) cultivating the transgenic plant under conditions enabling the expression of the two fructosyltransferase enzymes during biosynthesis of the fructan;

(e) isolating the fructan from the transgenic plant.

This method is useful in host plants that do not synthesize fructans in their wildtype state.

The method also includes producing fructans in the plant that have a low degree of polymerisation (DP) such that the isolated carbohydrate has a DP of 3 or above.

The carbohydrate can also be formed at least in part from isokestose produced by a 1-SST gene.

This carbohydrate may be formed at least in part by fructan biosynthesis based on a 1-kestose substrate.

The invention also provides a nucleic acid selected from the group consisting of a 1-SST gene, a 6-SFT gene, or a 6G-FFT gene.

Bacterial genes encoding fructosyltransferase produce higher levels of polymerisation compared to plant genes which encode fructosyltransferase.

The invention also provides a method for producing seeds of transgenic plants, which accumulate fructans having a degree of polymerisation at or above DP3, comprising the steps of:

(a) selecting two different nucleic DNA that code respectively for two fructosyltransferase enzymes that mediate the biosynthesis of a fructan having a low degree of polymerization;

(b) linking the DNA to suitable transcription-initiation and transcription-termination signals to provide an expression construct;

(c) transforming a suitable plant cell with the expression construct regenerating a transgenic plant from the transformed plant cell;

(d) cultivating the transgenic plant under conditions enabling the expression of the two fructosyltransferase enzymes;

(e) producing seed of transgenic plants, which express the two-fructosyltransferase enzymes.

Additional steps can include selecting, screening, or testing seed from said transgenic plant. The crossing of progeny to produce 1-SST, 6-SFT and 6G-FFT genes within the same plant and producing seed therefrom are also within the scope of this invention.

The invention also provides a transgenic plant which accumulates fructans having a fructosyltransferase activity expressed as a percentage of the degree of polymerization at or above DP2 comprising: two different nucleic acids operatively linked to a suitable transcription-initiation and transcription-termination signals which encode two fructosyltransferases capable of converting at least one substrate into a fructan having at least a DP2.

The present invention also provides a transgenic plant which accumulates a range of carbohydrates as fructans prepared from a host plant that does not normally accumulate fructans, said plant comprising fructans having a degree of polymerization of 2, 3, 4, and/or 5, wherein at least two different nucleic acids encoding fructosyltransferase that are present in the transgenic plant are not present in the wildtype host plant.

The transgenic plant may have has a larger percentage of DP2 than DP3 or a larger percentage of DP3 than DP2 or a larger percentage of DP3 than DP4.

The present invention also provides a transgenic plant comprising at least two genes that encode fructosyltransferase, wherein the fructosyltransferase activity has at least one degree of polymerization above DP 2.

The present invention can be formed in a plant which is a Dicot that is non-fructan accumulating, such as a sugar beet.

DETAILED DESCRIPTION

Application

There is a growing interest in using fructans as functional food ingredients. Fructans cannot be digested by enzymes in the human gut, and when they reach the colon they serve as a substrate for enterobacterial growth such as bifisobacteria which ferment fructans to short-chain fatty acids that have a positive effect on systemic lipid metabolism. The non-digestible nature of fructans makes them function as dietary fibers that have a bland flavor and a fat-like texture which are also useful as bulking agents for the production of low calorie foods and low calorie sweeteners. Fructans may also be valuable in animal nutrition. Transgenic plants synthesizing fructans therefore may improve animal performance.

Currently the most agronomically acceptable crop for fructan production is chicory although their function is limited by the degradation of long fructan chains by fructan exohydrolase during harvesting. Transformation of fructosyltransferases into agronomically-important crops, such as sugarbeet, holds great potential as sources of fructan with a range of structurally different fructan molecules.

Plants which are modified to accumulate fructans may be protected from water and cold stress.

The genes of the present invention can be synthetic or altered, or the native gene founded in bacteria or plant material. The present invention is also directed to use genes of vegetative origin such as those found in Poaceae, Liliaceae, and Asteracea. Genes for vegetable fructosyltransferases, for example, can be isolated and transgenic plants can be prepared by known methods.

Standard methods for cloning, which include methods related to the formation of vectors that propagate in yeast, bacteria, and plants, methods for isolation, and amplification of DNA, as well as use of suitable plasmids, selection markers, media, and the like, are described in Molecular Cloning: A Laboratory Manual. Cold Spring Harbor Laboratory Press, Cold Spring Harbor, N.Y. (1996).

Many plants can be transformed routinely with the vectors or DNA constructs described above, by several methods, including polyethylene glycol transformation of plant protoplasts (Krens et al. (1982), Nature 296, 72; Negrutiu et al. (1987), Plant Mol. Biol. 8, 363), electroporation of plant protoplasts (Shillito et al. (1985), Bio/Technol. 3, 1099), microinjection into plant materials (Crossway et al. (1986), Mol. Gen. Genet. 202), particle bombardment of various plant materials (Klein et al. (1987), Nature 327, 70), *Agrobacterium tumefaciens*-mediated DNA transfer, transformation of mature pollen or microspores as disclosed in EP 0 301 316, U.S. Pat. Nos. 5,464,765; 5,302,523, and the like. Transformation of lettuce, *Lattuca sativa* cv. Evola is described by Curtis et al. (1994) J. Exp. Bot. 45, 1441. Transformation of *Arabidopsis thaliana* may be performed by the method of Clarke et al. (1992) Plant Mol. Biol. Rep. 10, 178 or by the method of Valvekens et al. (1988) Proc. Natl. Acad. Sci. USA, 85, 5536. Transformation of sugar beets is described by D' Halluin et al. (Biotechnology 10, 309-314, 1992). Transformation of potatoes was described by Visser Plant, (Tissue Culture Manual b5, 1-9 Kluwer Academic Publishers, 1991). Transformation of *Brassica Napus* L. is taught by Block et al. (Plant Physiol. 91, 694-701, 1989).

Many plants are amenable to transformation, and fertile transgenic plants can be regenerated from transformed cells, such as microspores, calli, embryos, explants suspension cells, or other plant material. The transformation systems enable the application of the present invention to both Monocots and Dicots although regeneration methods vary from species to species of plants. Shoots are usually developed from callus by organogenesis or embryogenesis, and planted after roots develop. Standard breeding techniques including sexual crossing can be used to move the trait into other plants. DNA sequences associated with or operatively linked to the trait producing genes (including marker genes), such as transcriptional initiation regions, targeting sequences, enhancers, leader sequences, introns, and translational enhancers signals (e.g., Alfalfa Mosaic Virus RNA4), may be added to obtain the desired expression. Any number of types of promoters can be employed, such as constitutive promoters (e.g., rice actin promoter), and inducible promoters. Promoters having regulated expression patterns, (e.g., developmentally or cell-type specific), may be used to control expression of the genes of the invention (e.g., 35 S Cauliflower Mosaic Virus Promoter (CaMV) and TR7).

Promoters having developmentally or cell type specific expression patterns may also be used, such as the polyubiquitin promoter, or sink-specific promoters, such as the palatine promoter or the sporamine promoter of sweet potato. The native fructosyltransferase regulatory sequences can also be used.

Marker genes linked to the genes of the invention may also be used. Commonly used marker genes include herbicide resistance genes (as antibiotic markers are not presently favoured) such as the gene encoding a 5-enolshikimate-3-phosphate synthase (EPSPS) which confers tolerance to glyphosate, the glutamine synthase gene which confers resistance to glutamine synthetase inhibitors like phosphinothricin (WO 87/05327), the acetyl transferase gene from *Streptomyces viridochromogenes* which confers resistance to the selective agent phosphinothricin (EP-A 275 957), and the bar gene conferring resistance against Bialaphos (e.g., WO 91/02071).

One embodiment of the invention relates to a construct comprising a targeting sequence for directing the fructosyltransferase to a selected cellular region. The targeting sequence of carboxypeptidase Y (cpy) gene, including its signal sequence and the vacuolar targeting sequence, can be employed to target proteins to the vacuole. Other signal or targeting sequences may also be used, such as apoplastic signals and signals that target the mitochondria, plastids, the cell wall, or the cytoplasm.

The invention includes recombinant DNAs which can be used in a transformed host which will express the trait at a higher level than expressed untransformed in the wildtype host. Host organisms can include, but are not limited to, grasses, flowers, trees, agricultural crops, forage and fruits. Exemplary host plants include tobacco, *Arabidoposis*, sugar beet, sugar cane, melons, squash, tomatoes, grasses, maize, white corn, sweet corn, popcorn, oats, barley, rice, *Brassicas*, wheat, cotton, peanuts, alfalfa, soybeans, roses, petunias, sunflowers, germaniums, lettuce, apple, pear, strawberry, broccoli, carrots, artichoke, onion, barley, sorghum, beans, chicory, and vining peas.

The transformed host may also have other traits. These traits may be present due to mutation, transformation or breeding, such as traits which confer resistance to disease, herbicides, fungus, insects, growth, stress, or drought tolerance, or altered reproductive traits, and the like. The present invention also relates to a plant. The term "plant" means all plant parts, including seedlings, roots, stems, seeds, oils, husks, kernels, flowers, stamen, anthers, petals, and parts that are on a cellular level like microspores and ovules and the like. The invention also includes the progeny of transformed plants of the invention that contain DNA of the invention stably incorporated into their genome, and seeds thereof.

The present invention also relates to transgenic plants which contain at least two of three genes encoding fructosyltransferase selected from 1-SST, 6-SFT, and 6G-FFT wherein the host plant without these genes does not produce fructans. The plants of the invention make fructans that differ in their physical and chemical properties compared to other unaltered plants or transgenic plants that produce fructans. Some of the properties changes are due to changes in their DP.

The transformed plants of the invention were assembled in the following manner:

Genes

1-SST: sucrose:sucrose 1-fructosyltransferase, isolated from onion (*Allium cepa*) by Vijn et al., 1998 sequences (as published) See SEQ. ID. No. 1:

1. SST Gene cDNA

Similar genes can be extracted from other fructan producing plants or be synthesized that would encode the fructosyltransferases described above.

Fructans (polyfructosylsucrose) consist of polymers of fructose attached to sucrose and serve as an important carbohydrate storage in approximately 15% of flowering plant species (Hendry and Wallace, 1993). The fructans are either linked by a (2-1)β-D-glycosidic bond, such as in inulin derived from *Cichorium intybus* L. (Bonnett et al, 1994), or by a (2-6)9-D-glycosidic bond as found in levans (Suzuki and Pollock, 1986). Branched fructans containing both types of linkages are produced in many grasses (Carpita et, al., 1989). A special type of fructan, the inulin neoseries, is produced in plants like onion. In these, the glycosidic moiety of sucrose contains fructosyl residues on both C1 and C6, resulting in a polymer with β(2-1)-D-linked fructosyl chains on either end of the sucrose molecule (Shiomi, 1989).

1-SST initiates de novo fructan synthesis by catalyzing the transfer of a fructosyl residue from sucrose to another sucrose molecule, resulting in the formation of the trisaccharide 1-kestose (G1-2F1-2F), also called isokestose. This molecule serves as donor or acceptor of fructosyl residues for the second enzyme.

6-SFT is the key enzyme for the biosynthesis of the branched type of fructans. 6-SFT produces 6-kestose (G1-2F6-2F) when only sucrose is present as substrate, but when both sucrose and 1-kestose are available, both bifurcose (G1-2F1(6-2F)-2F) is produced.

For the production of the inulin neoseries, 6G-FFT is needed. This fructosyltransferase catalyzes the transfer of a fructose residue of 1-kestose to C6 of the glycosidic moiety of sucrose, forming neokestose (F2-6G1-2F).

The following examples are provided to illustrate the invention and are not to be viewed as a limitation of the scope of the invention.

EXAMPLE 1

Constructs

The structural genes indicated as SEQ ID NOS. 1-3 encoding the three fructosyltransferases were inserted into a pUC19 derived vector, between the ubiquitin promoter from *Arabidopsis thaliana* and the polyadenylation signal sequence derived from the nopaline synthase gene of *Agrobacterium tumefaciens*.

Figure 1:
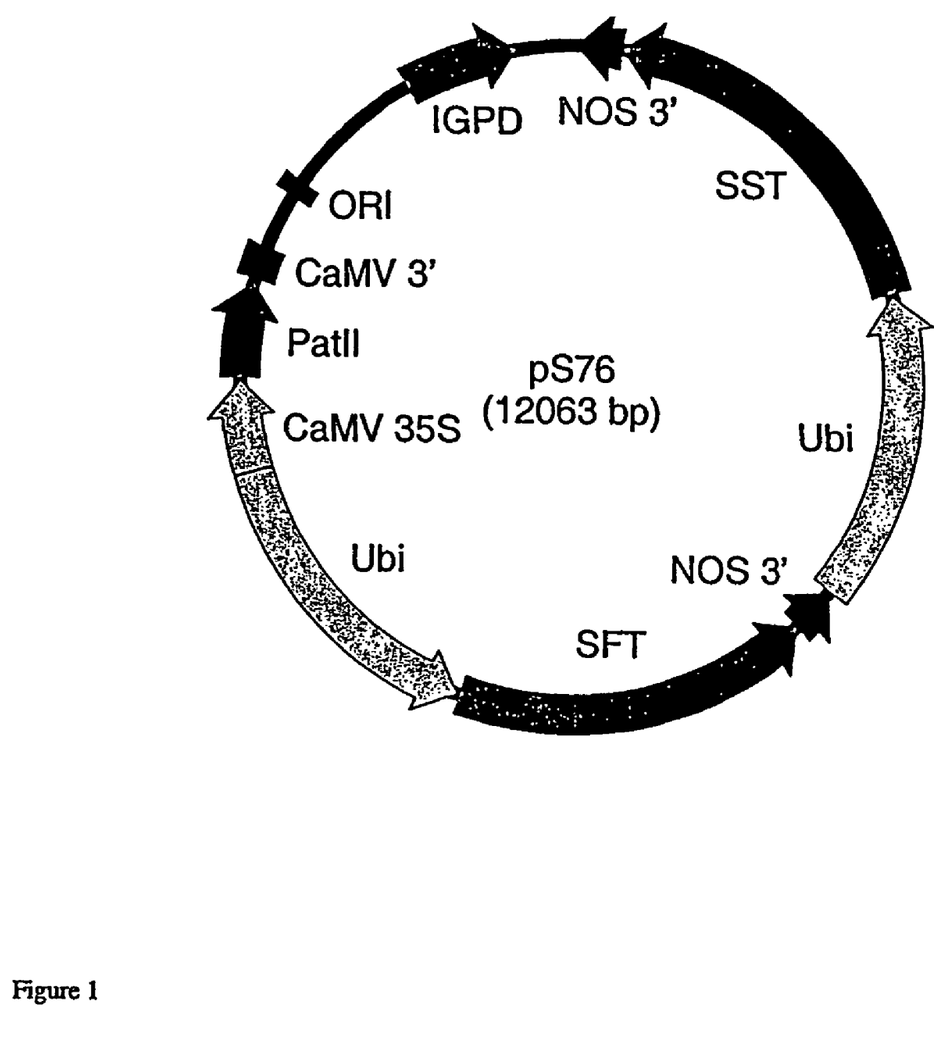
FIG. 1 the construction of the transformation vector pS76.

To construct the transformation vector pS76, the ubiquitin-SST-Nos3' expression cassette was excised as a NotI fragment and inserted into a pIGPD7 derivative, where the NcoI site had been modified into a NotI site. The resulting construct, pVDH593, contained the pat and the SST gene with their regulatory elements. The ubiquitin-SF-Nos3' expression cassette was then excised as a NotI fragment and inserted into the NotI site of a partially-digested pVDH593 to create pS76.

Figure 2:
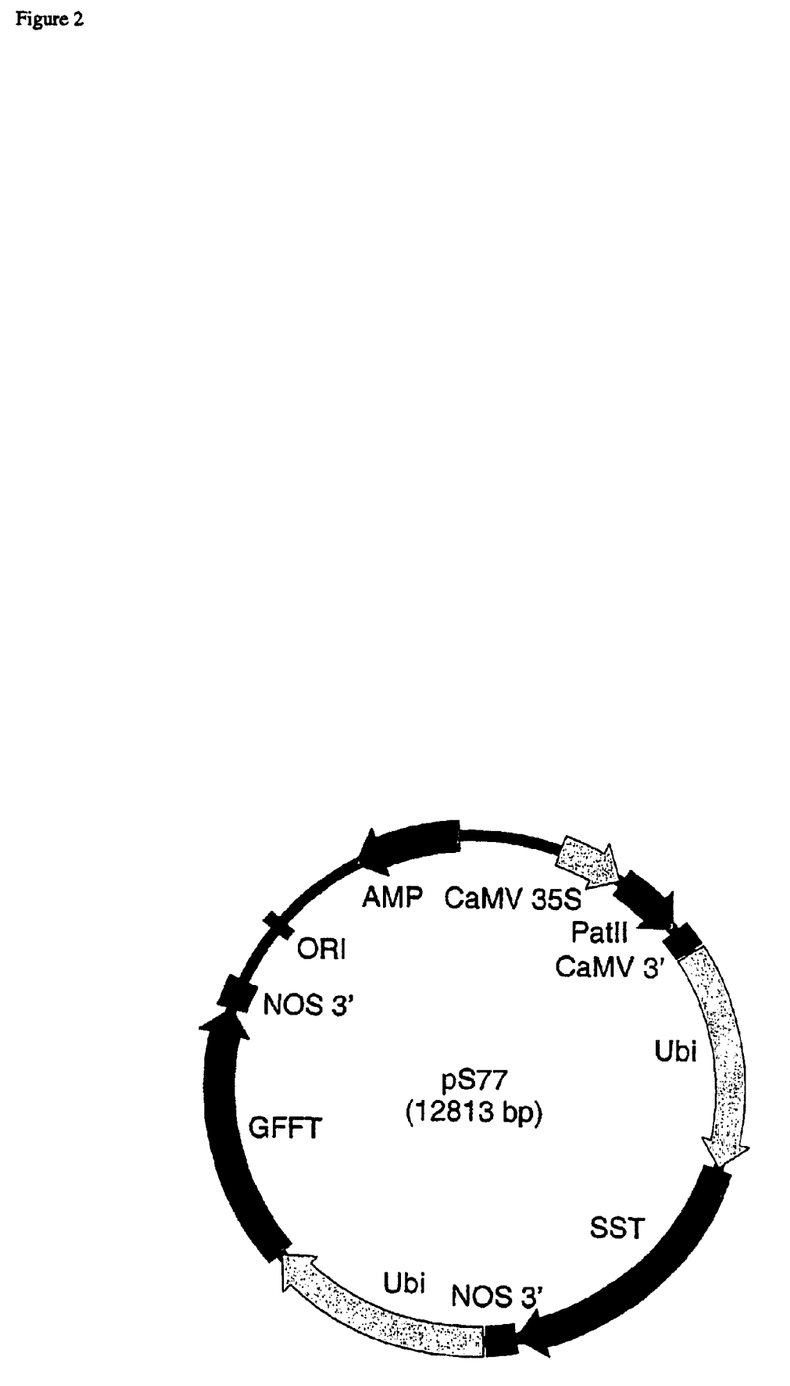
FIG. 2 the construction of the transformation vector pS77.

To construct the transformation vector pS77, the pat gene, under the transcriptional control of the CaMV 35S promoter and the CaMV 35S polyadenylation signal was excised as an EcoRI fragment. A NotI linker was fused to this fragment and subcloned into pVDH602, containing tandem ubiquitin-SST-Nos3' and ubiquitin-GFFT-Nos3' expression cassettes, partially digested with NotI. This resulted in pS77.

EXAMPLE 2

Transformation of Sugar Beet

A previously developed protocol (described in WO 95/10178 incorporated herein by reference) for the isolation and purification of guard cell protoplasts was followed to obtain large numbers of >90% pure sugar beet guard cell protoplasts. Guard cell protoplast yields are routinely 1-3× $10^6$/g leaf material.

PEG-mediated transformations with 50 μg plasmid DNA (pS76 or pS77)/1×$10^6$ protoplasts were performed. Protoplasts were embedded in $CA^{++}$ alginate (62500/ml and cultured in modified, liquid K8P medium. To select for stably transformed cells, bialaphos was added after seven days at a final concentration of 200 μg/l. The resistant calli, grown out of the alginate, were transferred onto fresh solidified selection medium. The calli were subsequently subcultured on non-selective medium and regeneration occurred via somatic embryogenesis. Finally, these somatic embryos were subcultured and they developed into plants. A total number of 105 independent transgenic sugar beet plants were obtained with plasmid pS76 and 223 independent transgenic plants with plasmid pS77.

EXAMPLE 3

Screening of the Ploidy of Transgenic Plants

The ploidy level of all transgenic plants was determined by flow cytometry. Only diploid material was kept for further analysis. The results are summarised in Table 1.

TABLE 1

Ploidy determination of the double fructan transgenic plants

| Construct # | independent transgenics | # diploid plants |
|---|---|---|
| pS76 | 105 | 69 |
| pS77 | 223 | 164 |

EXAMPLE 4

Analysis of Sugars and Fructans

One of ordinary skill in the art would recognize that there are various means and methods for analyzing sucrose and fructans. For example, sucrose and fructans can be analyzed with a RP-HPLC using a 2.1×220 mm Speri-5 RP 18 column (Brownlee Labs, Santa Clara, USA). Milli Q water may be used as the eluant at a flow rate of 0.3 $cm^3$ $min^{-1}$ at 37° C. Glucose and fructose may quantified on a 6.5×300 mm Shodex SC-1011 column (Millipore B. V., Waters Chromatography Division, The Netherlands). If this is employed, it may be run at 85° C. with Milli Q water at 0.75 $cm^3$ $min^{-1}$. Sugars are detected for example by a 2142 refraction index detector (RID, Pharmacia). Fructans are compared with retention times of the purified controls and thus Identified according to (Koops and Jonker, 1994).

Neutral carbohydrates may be analysed by means of anion exchange chromatography. High performance anion exchange chromatography analyses of oligofructans and fructans with a higher degree of polymerization may also be performed, for example, on a Dionex Series 4000 ion chromatograph equipped with 250×4 mm CarboPac PA100 anion exchange column (Dionex, Sunnyvale, Calif. USA) and with a Dionex DX-300 gradient chromatography system coupled to pulsed amperometric detection. The applied potential of a pulse is monitored. An internal standard is employed. Fructans retention times are compared with those of fructan standards isolated and purified according to, for instance, the method of Heinze and Praznik in the Journal of Applied Polymer Science: Applied Polymer Symposium 48, 207-225 (1991).

In order to identify the transgenic plants that express the fructosyltransferase, these leaf extracts were analysed by Shodex. Approximately 2 to 3 g leaf material from the in vitro grown plantlets was harvested, freeze dried and grinded. An equal volume of water was added, mixed and incubated at 80-85° C. for 5-10 minutes. After centrifugation at 14000 rpm for 5-10 minutes, the degree of fructosyltransferase activity was determined as the percentage of DP3 (degree of polymerization) by high performance liquid chromatography (HPLC) using a Shodex KS-802, 300×8 mm (Waters) column. Candidates with a DP3 percentage equal or above 0.03% were kept. The results are given in Table 2.

(HPLC) using a Shodex KS-802, 300×8 mm (Waters) column. Candidates with a DP3 percentage equal or above 0.03% were kept. The results are given in Table 2.

TABLE 2

Identification of fructan producing plants

| Construct | # plants analysed | # plants with DP3 => 0.03% |
|---|---|---|
| pS76 | 69 | 8 |
| pS77 | 164 | 15 |

Plantlets which were identified with a DP3 value of 0.03% were rooted and transferred to the greenhouse.

Eight independent transgenic plants containing the SST and SFT genes were encoded SSF34, SSF37, SSF48, SSF60, SSF66, SSF76, SSF100 and SSF104. Fifteen independent transgenic plants containing the SST and GFFT genes were encoded SSG2, SSG25, SSG32, SSG39, SSG100, SSG107, SSG128, SSG134, SSG135; SSG166, SSG171, SSG175, SSG184, SSG188 and SSG190.

From these plants, two roots were harvested at 3, 4 and a half, and at 6 months.

A Shodex analysis confirmed the leaf results indicated above. The analysis clearly indicated that apart from DP3, DP4, DP5 and longer fructan chains were synthesized.

Figure 3:
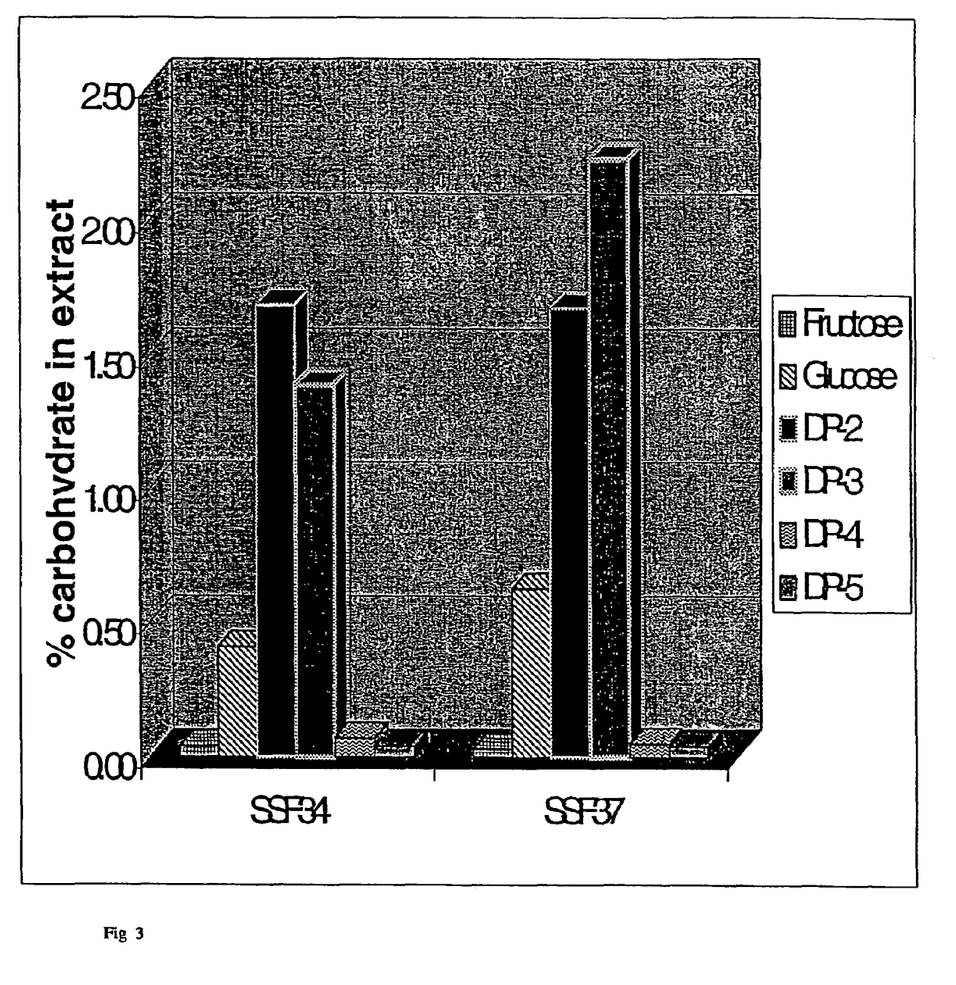
FIG. 3 shows the levels DP2, DP3, DP4 and DP5 for SSF34 and SSF37.
Figure 4:
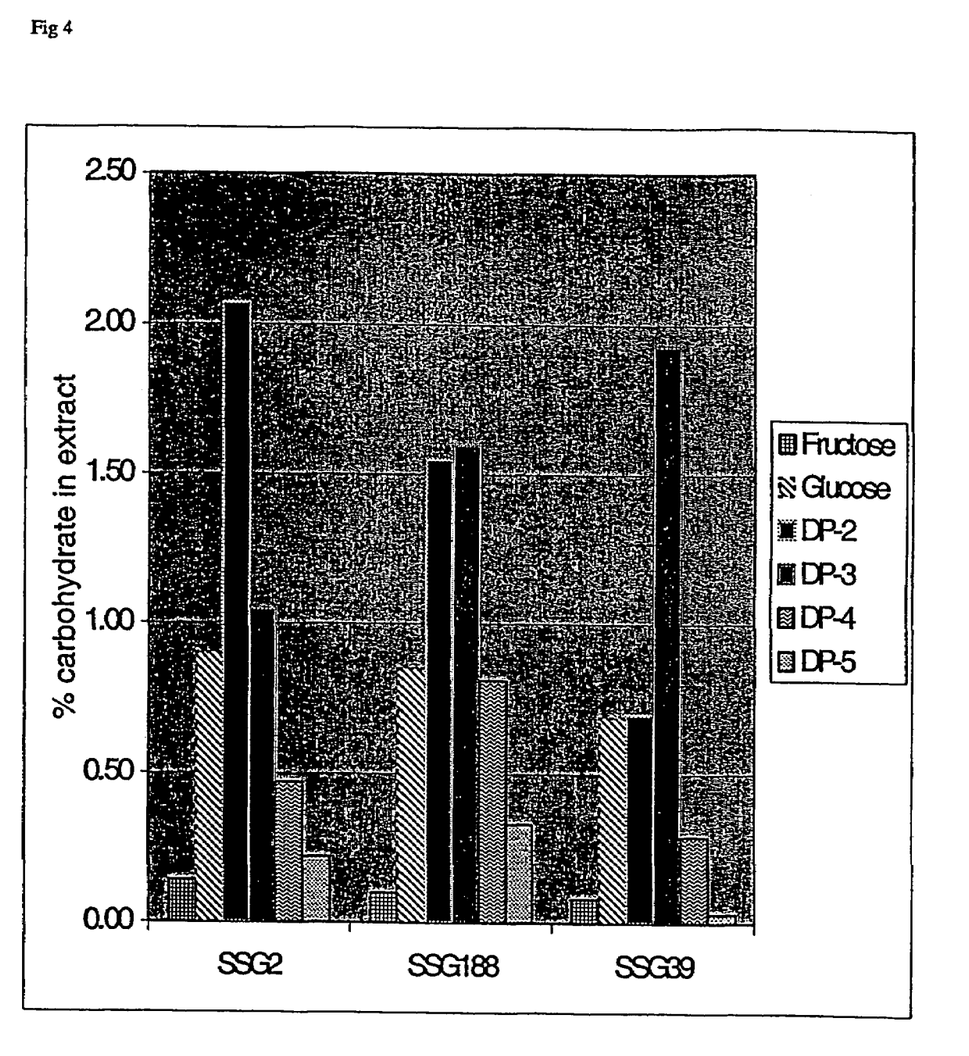
FIG. 4 shows the levels DP2, DP3, DP4 and DP5 for SSG2, SSG39 and SSG188.
Figure 5:
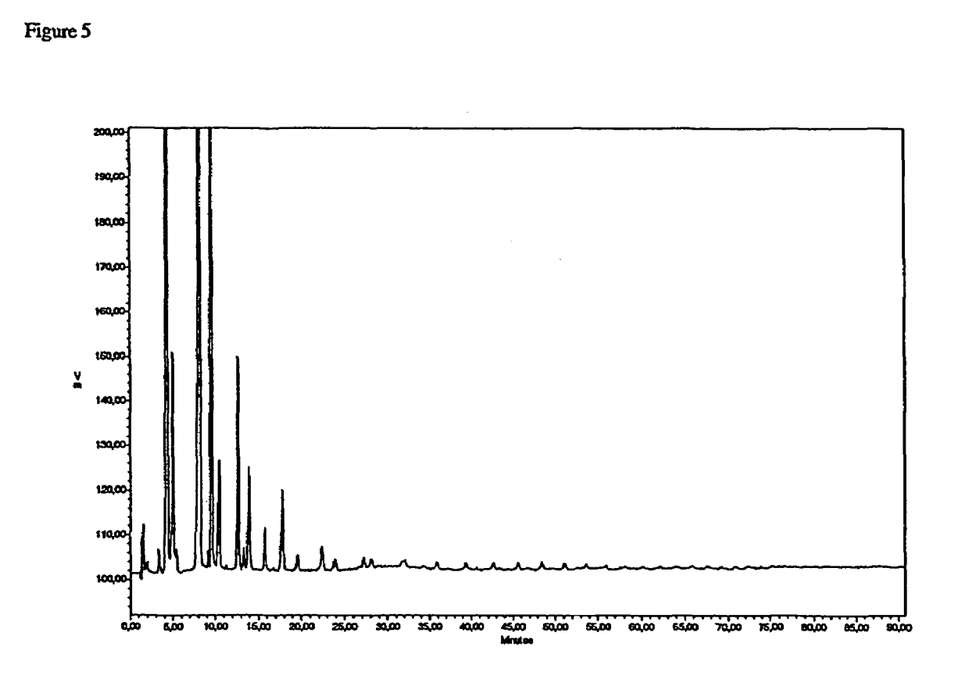
FIG. 5 is a Dionex pattern of SSF34 displaying the presence of longer fructan chains.
Figure 6:
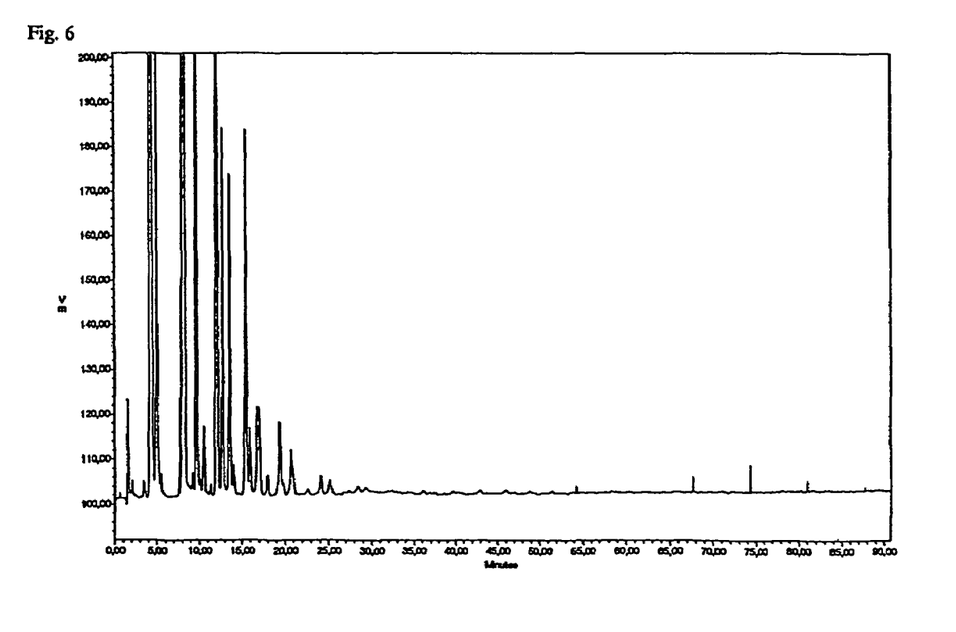
FIG. 6 is a Dionex patterns of SSG2, displaying the presence of longer fructan chains.

FIG. 3 shows the levels DP2, DP3, DP4 and DP5 for SSF34 and SSF37. FIG. 4 shows the levels DP2, DP3, DP4 and DP5 for SSG2, SSG39 and SSG188. FIGS. 5 and 6 are Dionex patterns of SSF34 and SSG2 respectively, displaying the presence of longer fructan chains.

Double Fructan Beet

Here we describe the integration and functional expression of a combination of two fructosyltransferase into sugarbeet, a plant that lacks fructans. Sugarbeet is a suitable crop for introducing fructan synthesizing enzymes because it accumulates a high percentage of sucrose in the vacuole. The first enzyme, 1-SST, initiates the fructan synthesis and produces 1-kestose, which is the substrate for the second enzyme, 6-SFT or 6G-FFT. These latter enzymes, in conjunction with the 1-SST, are responsible for the accumulation of higher DP fructans by the elongation of the isokestose produced by the 1-SST. The action of both enzymes results in the formation of a mixture of fructan molecules with different chain lengths.

Analysis of the different transgenic beets clearly indicate the presence of 1-kestose (as high levels of DP3). Furthermore, DP4, DP5 and higher fructans demonstrate that the second enzyme is also active. In addition to 1-kestose, 1-SST is able to produce tetra and even pentasaccharides but not long chain fructans. This is also visible in comparison to transgenic plants expressing 1-SST only (data not shown).

Compared to the SST-beet from Wageningen, these double fructan transformants lead to beet with higher DPs. This is more pronounced in the 1-SST/6G-FFT material than in the 1-SST/6-SFT plants.

Bonnett, G., Sims, I., John, J. and Simpson, R. (1994) New Phytol. 127: 261-269

Carpita, N., Kanabus, J. and Housley, T. (1989) J. Plant Physiol. 134: 162-168

Hendry G. and Wallace, R. (1993) In M. Suzuki, N J Chatterton, eds, Science and Technology of Fructans. CRC Press, Boca Raton, Fla., 119-139

Shiomi, N. (1989) J. Plant Physiol. 134:151-155

Sprenger, N., Bortlik, K., Brandt, A, Boller, T. and Wiemken, A (1995) Proc. Natl. Acad. Sci. USA 92: 11652-11656

Suzuki, M. and Pollock, C. (1986) Can. J. Bot. 64: 1884-1887

Vijn, I., van Dijken, A., Sprenger, N., van Dun, K., Weisbeek, P., Wiemken, A. and Smeekens, S. (1997) Plant J. 11: 387-398

Vijn, I., van Dijken, A., Luscher, M., Bos, A., Smeets, E., Weisbeek, P., Wiemken, A. and Smeekens, S. (1998) Plant Physiol. 117: 1507-1513

What is claimed is:

1. A method for producing fructans having a degree of polymerization (DP) of from DP2 to DP5, comprising the steps of:
   (a) selecting two genes of plant origin which encode different fructosyltransferase enzymes, wherein the two different fructosyltransferase enzymes are 1-SST and 6G-FFT or 1-SST and 6-SFT;
   (b) operably linking the genes to suitable transcription-initiation and transcription-termination signals to provide an expression construct;
   (c) transforming a sugar beet or sugarcane host plant cell with the expression construct;
   (d) regenerating a transgenic plant from the transformed plant cell;
   (e) cultivating the transgenic plant under conditions enabling the expression of the two fructosyltransferase enzymes during biosynthesis of the fructans; and
   (f) isolating the fructans from the transgenic plant, wherein the percentage of DP3 is greater than DP2.

2. The method of claim 1 wherein the isolated fructan has a DP of 3 or above.

3. The method of claim 1 wherein the isolated fructan has a DP of 3 or above formed at least in part from isokestose produced by a 1-SST gene.

4. The method of claim 1 wherein the isolated fructan has a DP of 3 or above and is formed at least in part from fructan synthesis based on a 1-kestose substrate.

5. A method for producing seeds of transgenic plants which accumulate fructans having a degree of polymerization (DP) at or above DP3, wherein the percentage of DP3 is greater than DP2, comprising the steps of:
   (a) selecting two genes of plant origin which encode different fructosyltransferase enzymes, wherein the two different fructosyltransferase enzymes are 1-SST and 6G-FFT or 1-SST and 6-SFT;
   (b) operably linking the genes to suitable transcription-initiation and transcription-termination signals to provide an expression construct;
   (c) transforming a sugar beet or sugarcane host plant cell with the expression construct;
   (d) regenerating a transgenic plant from the transformed plant cell;
   (e) cultivating the transgenic plant under conditions enabling the expression of the two fructosyltransferase enzymes; and
   (f) producing seed of transgenic plants which express the two fructosyltransferase enzymes.

6. A transgenic plant which accumulates fructans having a degree of polymerization (DP) at or above DP2 comprising: two genes of plant origin which encode different fructosyltransferase enzymes, wherein the two different fructosyltransferase enzymes are 1-SST and 6G-FFT or 1-SST and 6-SFT, operably linked to a suitable transcription-initiation and transcription-termination signal to provide an expression construct which encodes fructosyltransferase enzymes which convert at least one substrate into a fructan having at least a DP2, wherein the transgenic plant is selected from sugar beet or sugarcane and wherein the percentage of DP3 is greater than DP2.

7. A transgenic plant comprising at least two different genes of plant origin which encode two different fructosyltransferase enzymes, wherein the two different fructosyltransferase enzymes are 1-SST and 6G-FFT or 1-SST and 6-SFT, operably linked to one or more suitable transcription initiation and transcription termination signals to provide an expression construct, wherein said transgenic plant expresses fructans having a degree of polymerization (DP) ranging from DP2 to DP5, and said transgenic plant is selected from sugar beet or sugarcane, and wherein the percentage of DP3 is greater than DP2.

8. The transgenic plant according to claim 7 wherein the percentage of DP3 is greater than DP4.

* * * * *

UNITED STATES PATENT AND TRADEMARK OFFICE
CERTIFICATE OF CORRECTION

PATENT NO. : 7,608,754 B2 Page 1 of 1
APPLICATION NO. : 10/415686
DATED : October 27, 2009
INVENTOR(S) : Weyens et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 720 days.

Signed and Sealed this

Twelfth Day of October, 2010

David J. Kappos
*Director of the United States Patent and Trademark Office*